(12) United States Patent
Tan et al.

(10) Patent No.: US 7,728,982 B2
(45) Date of Patent: *Jun. 1, 2010

(54) FIBER-OPTIC ASSAY APPARATUS BASED ON PHASE-SHIFT INTERFEROMETRY

(75) Inventors: Hong Tan, San Jose, CA (US); Yushan Tan, Shanghai (CN); Duan Jun Chen, East Brunswick, NJ (US); Krista Leah Witte, Hayward, CA (US)

(73) Assignee: ForteBio, Inc., Menlo Park, CA (US)

( * ) Notice: Subject to any disclaimer, the term of this patent is extended or adjusted under 35 U.S.C. 154(b) by 39 days.

This patent is subject to a terminal disclaimer.

(21) Appl. No.: 12/099,751

(22) Filed: Apr. 8, 2008

(65) Prior Publication Data

US 2008/0186505 A1 Aug. 7, 2008

Related U.S. Application Data

(63) Continuation of application No. 10/981,901, filed on Nov. 4, 2004, now Pat. No. 7,394,547.

(60) Provisional application No. 60/518,068, filed on Nov. 6, 2003, provisional application No. 60/558,381, filed on Mar. 31, 2004.

(51) Int. Cl.
*G01B 9/02* (2006.01)

(52) U.S. Cl. .................................. 356/478; 356/480

(58) Field of Classification Search ............ 356/478, 356/480, 519
See application file for complete search history.

(56) References Cited

U.S. PATENT DOCUMENTS

| | | | |
|---|---|---|---|
| 4,830,451 A | 5/1989 | Stone | |
| 5,301,001 A | 4/1994 | Murphy et al. | |
| 5,359,405 A | 10/1994 | Andrews | |
| 5,422,970 A | 6/1995 | Miller et al. | |
| 5,425,039 A | 6/1995 | Hsu et al. | |

(Continued)

FOREIGN PATENT DOCUMENTS

WO    WO 2004/025282 A    3/2004

OTHER PUBLICATIONS

Brecht et al, Direct monitoring of antigen-antibody interactions by spectral interfrometry, Sensors and actuators B, vol. 6, 1992, pp. 96-100.*

(Continued)

*Primary Examiner*—Samuel A Turner
(74) *Attorney, Agent, or Firm*—Fenwick & West LLP

(57) ABSTRACT

Apparatus and method for detecting the presence or amount or rate of binding of an analyte in a sample solution is disclosed. The apparatus includes an optical assembly having first and second reflecting surfaces separated by a distance "d" greater than 50 nm, where the first surface is formed by a layer of analyte-binding molecules, and a light source for directing a beam of light onto said first and second reflecting surface. A detector in the apparatus operates to detect a change in the thickness of the first reflecting layer resulting from binding of analyte to the analyte-binding molecules, when the assembly is placed in the solution of analyte, by detecting a shift in phase of light waves reflected from the first and second surfaces.

35 Claims, 6 Drawing Sheets

U.S. PATENT DOCUMENTS

| | | | |
|---|---|---|---|
| 5,452,087 | A | 9/1995 | Taylor et al. |
| 5,528,367 | A | 6/1996 | Putnam et al. |
| 5,594,819 | A | 1/1997 | Narendran et al. |
| 5,606,170 | A | 2/1997 | Saaski et al. |
| 5,647,038 | A | 7/1997 | Minden et al. |
| 5,682,237 | A | 10/1997 | Belk |
| 5,701,193 | A | 12/1997 | Vogel et al. |
| 5,732,169 | A | 3/1998 | Riant et al. |
| 5,804,453 | A * | 9/1998 | Chen .......................... 356/478 |
| 5,869,835 | A | 2/1999 | Udd |
| H1813 | H | 11/1999 | Kersey |
| 5,982,959 | A | 11/1999 | Hopenfeld |
| 6,055,080 | A | 4/2000 | Furstenau et al. |
| 6,078,706 | A | 6/2000 | Nau et al. |
| 6,139,797 | A | 10/2000 | Suzuki et al. |
| 6,241,397 | B1 | 6/2001 | Bao et al. |
| 6,244,214 | B1 | 6/2001 | Hebrank |
| 6,248,539 | B1 | 6/2001 | Ghadiri et al. |
| 6,254,830 | B1 | 7/2001 | Pivarnik et al. |
| 6,275,628 | B1 | 8/2001 | Jones et al. |
| 6,277,651 | B1 | 8/2001 | Groger et al. |
| 6,281,976 | B1 | 8/2001 | Taylor et al. |
| 6,445,838 | B1 | 9/2002 | Caracci et al. |
| 6,496,618 | B1 | 12/2002 | Fernando et al. |
| 6,539,136 | B1 | 3/2003 | Dianov et al. |
| 6,571,639 | B1 | 6/2003 | May et al. |
| 6,590,665 | B2 | 7/2003 | Painchaud et al. |
| 6,611,334 | B1 | 8/2003 | Fernando et al. |
| 6,661,520 | B1 | 12/2003 | Lin et al. |
| 6,671,055 | B1 | 12/2003 | Wavering et al. |
| 6,687,011 | B1 | 2/2004 | Lee et al. |
| 6,720,177 | B2 | 4/2004 | Ghadiri et al. |
| 6,744,939 | B2 | 6/2004 | Lampert et al. |
| 7,158,225 | B2 | 1/2007 | Tedesco et al. |
| 7,319,525 | B2 | 1/2008 | Tan et al. |
| 7,394,547 | B2 * | 7/2008 | Tan et al. .................... 356/480 |
| 2001/0048072 | A1 | 12/2001 | Painchaud et al. |
| 2003/0112443 | A1 * | 6/2003 | Hjelme et al. ............... 356/480 |
| 2004/0022475 | A1 | 2/2004 | Pennington |
| 2004/0186359 | A1 | 9/2004 | Beaudoin et al. |

OTHER PUBLICATIONS

Brecht et al, Recent developments in optical transducers for chemical or biological applications, Sensors and actuators B, vol. 38-39, 1997, pp. 1-7.*

Yang et al, Direct monitoring of antigen-antibody interactions by opticsl fiber bioprobe, Proc. of SPIE, vol. 5254, 2003, 431-436.*

Boiarski, A. et al., "Integrated-Optic Biosensor", SPIE, Fiber Optical Sensors in Medical Diagnostics, vol. 1886, 1993, pp. 15-26.

Brecht, A. et al., "Direct Monitoring of Antigen-Antibody Interactions by Spectral Interferometry", Sensors and Actuators, vol. B5, 1992, pp. 96-100.

Brecht, A. et al., "Interferometric Immunoassay in a FIA-System: a Sensitive and Rapid Approach in Label-free Immunosensing", Biosensors & Bioelectronics, vol. 8, 1993, pp. 387-392.

Brecht, A., et al., "Recent Developments in Optical Transducers for Chemical or Biochemical Applications," Sensors and Actuators B, Jan. 1997, pp. 1-7, vol. 38, No. 1-3.

Brecht, A. et al., "Theoretical and Experimental Detectivity of the RIFS—transducer in Affinity-sensing", Biosensors 94, The Third World Congress on Biosensors: Abstracts, Oral Session, Jun. 2, 1994, p. 68.

Cao, L. et al., "Detection of Yersinia Pestis Fraction 1 Antigen With a Fiber Optic Biosensor", Journal of Clinical Microbiology, vol. 33, No. 2, Feb. 1994, pp. 336-341.

Chinese Application No. 20040031823.5 Office Action, Jul. 20, 2007, 16 pages.

Christensen, D. et al., "Analysis of Excitation and Collection Geometries for Plannar Waveguide Immunosensors," SPIE vol. 1886, Fiber Optic Sensors in Medical Diagnostics, 1993, pp. 2-8.

Davies, R. et al., "An Optical Biosensor System for Molecular Interaction Studies", American Biotechnology Laboratory, Jul. 1993.

Elster, J. L. et al., "Optical Fiber Extrinsic Fabry-Perot Interferometric (EFPI)-Based Biosensors," Proceedings of the SPIE, 2000, pp. 105-112, vol. 3911.

European Examination Report, EP 04800761.1, Nov. 23, 2007, 5 pages.

European Supplementary Search Report, EP 04800761, Mar. 19, 2007, 4 pages.

Fabricius, N. et al., "A Gas Sensor Based on an Integrated Optical Mach-Zehnder Interferometer", Sensors and Actyators, vol. B7, 1992, pp. 672-676.

Gauglitz, G. et al., "Observation of Spectral Interferences for the Determination of Volume and Surface Effects of Thin Films", Analytical Biochemistry, vol. 341, 1991, pp. 279-283.

Gauglitz, G. et al., "Recent Developments in Optical Transducers for Chemical or Biochemical Applications," Sensors and Actuators B, Jan. 1997, pp. 1-7, vol. 3-39, Elsevier Science S.A., Lausanne, CH.

Hogg, D. et al., "Development of a Fiber Fabry-Perot Strain Gauge", SPIE vol. 1588, Fiber Optic Smart Structures and Skins IV, 1991, pp. 300-307.

International Search Report and Written Opinion, PCT/US06/22964, Jun. 1, 2007, 9 pages.

Jorgenson, R. et al. "A Novel Surface Plasmon Resonance Based Fiber Optic Sensor Applied to Biochemical Sensing", SPIE, vol. 1886, 1993, pp. 35-48.

Kimoshita, Y. et al., "Sensing of Herbicide Residues Using Surface Plasmon Resonance Technique", The Third World Congress on Biosensors: Abstracts, 1994, p. 257.

Lin, C-J., et al., "A Novel in Vitro and in Situ Immunoassay Biosensor Based on Fiber Optic Fabry-Perot Interferometry," Proceedings of the SPIE, The International Society for Optical Engineering, 2004, pp. 304-307, vol. 5502, No. 1.

Lukosz, W., et al., "Output grating Coulers on Planar Optical Waveguides as Direct Immunosensors", Biosensors & Bioelectronics, vol. 6, 1991, pp. 227-232.

Lundstrom, I., et al. "Immunosensors Based on Surface Plasmon Resonance", The Third World Congress on Biosensors: Abstracts, 1991, p. 91.

PCT International Search Report and Written Opinion, PCT/US06/22964, Jun. 1, 2007, 9 pages.

PCT International Search Report and Written Opinion; PCT/US04/36830, Sep. 6, 2005, 9 pages.

Rudraraju, S. et al., "Acoustic Wave Propagation in Composite Materials: an Experimental Study", SPIE, vol. 2191, Jul. 1994, pp. 487,493.

Schneider, I. et al., "Herbicide Detection Using Reaction, Centers Integrated Into Liposomes Binding to Grating Couplers", The Third World Congress on Biosensors: Abstracts, 1994, p. 271.

Weber, A. et al., "Fiber-optic Fluorimetry in Biosensors: Comparison Between Evanescent Wave Generation and Distal-face Generation of Fluorescent Light", Biosensors & Bioelectronics, vol. 7, 1992, pp. 193-197.

Yang Y et al., "Direct Monitoring of Antigen-Antibody Interactions by Optical Fiber Bioprobe," Proceedings of the SPIE, Jun. 8, 2003, pp. 431-436, vol. 5254, No. 1.

Yang, Y. et al., "Study of Optical Fiber Biosensor Based on White-Light Interferometry," Journal of Xi'An Jiaotong University, Sep. 2003, pp. 914-916, 988, vol. 37, No. 9, Xian, CN.

Supplementary European Search Report for European Patent Application No. EP 06784824, Feb. 23, 2009, 6 pages.

European Search Report for European Patent Application No. EP 08018376.7, Jan. 21, 2009, 18 pages.

* cited by examiner

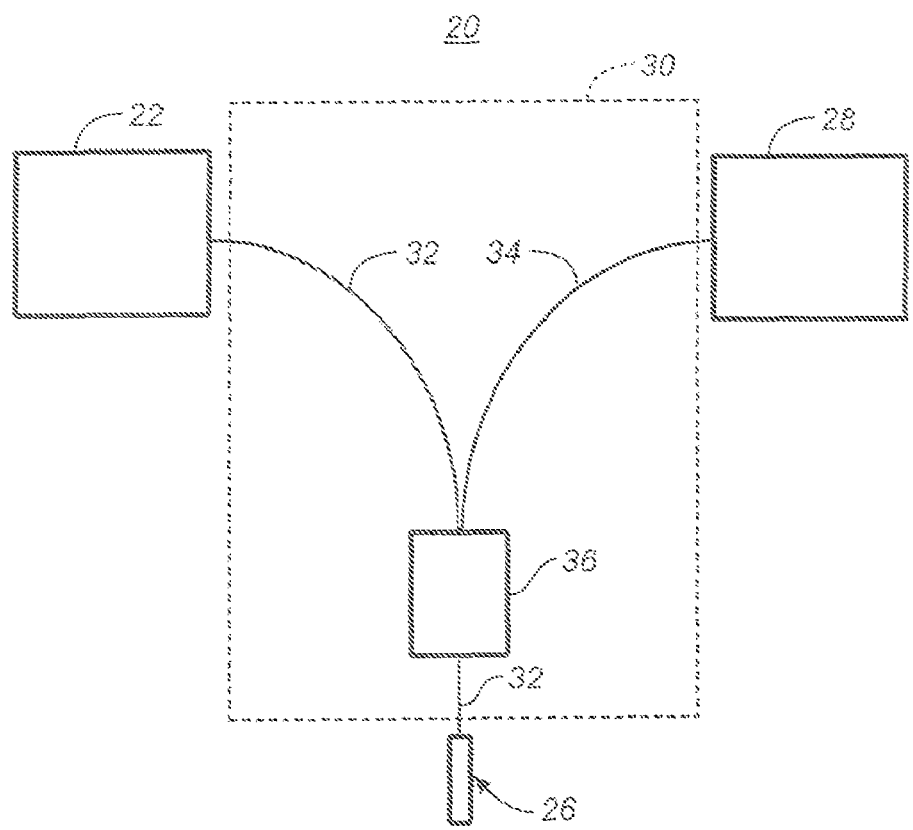
FIG._1
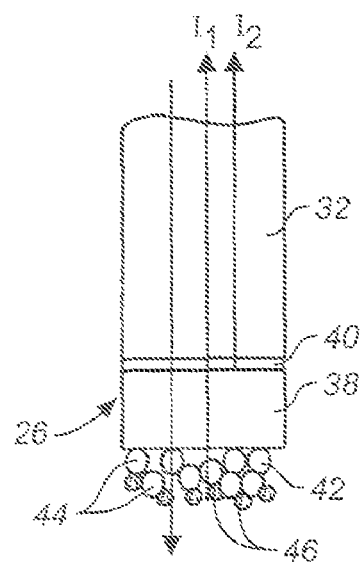
FIG._2

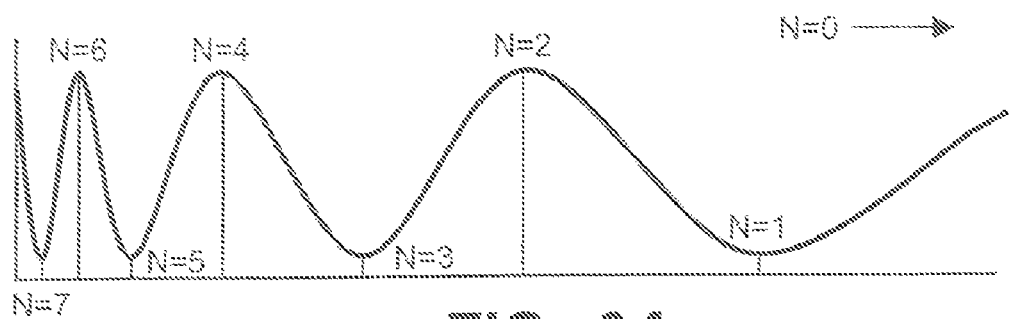
FIG._3A
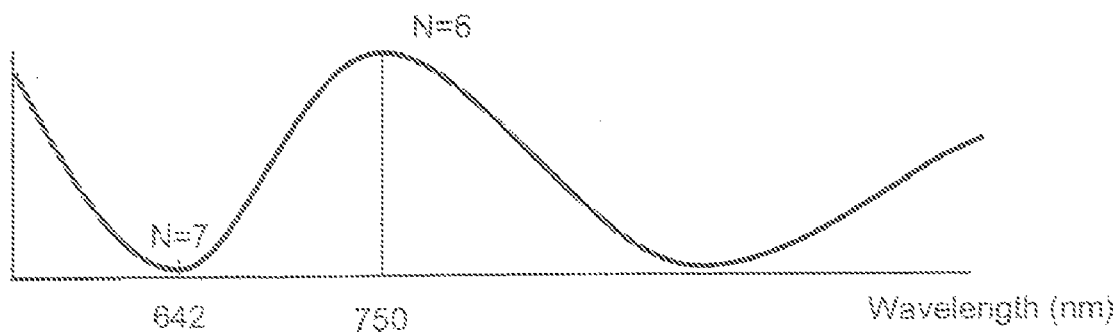
FIG._3B
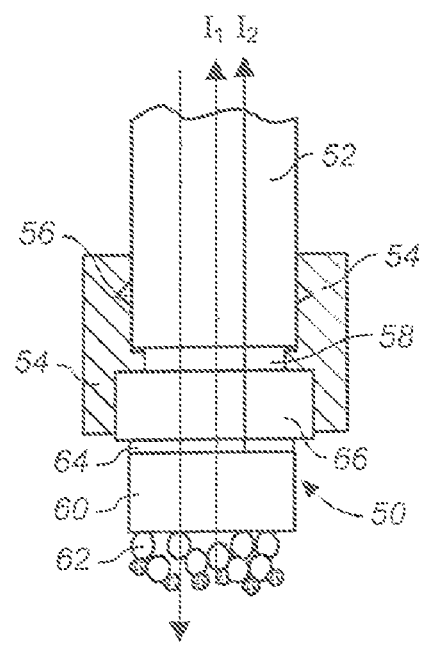
FIG._4

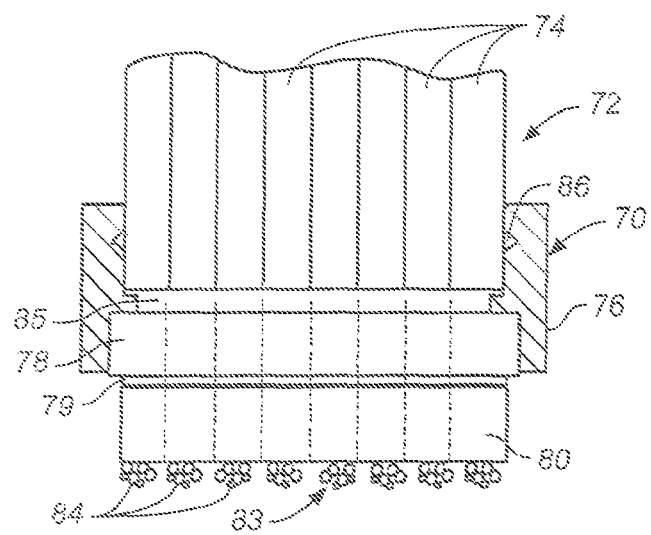
FIG._5
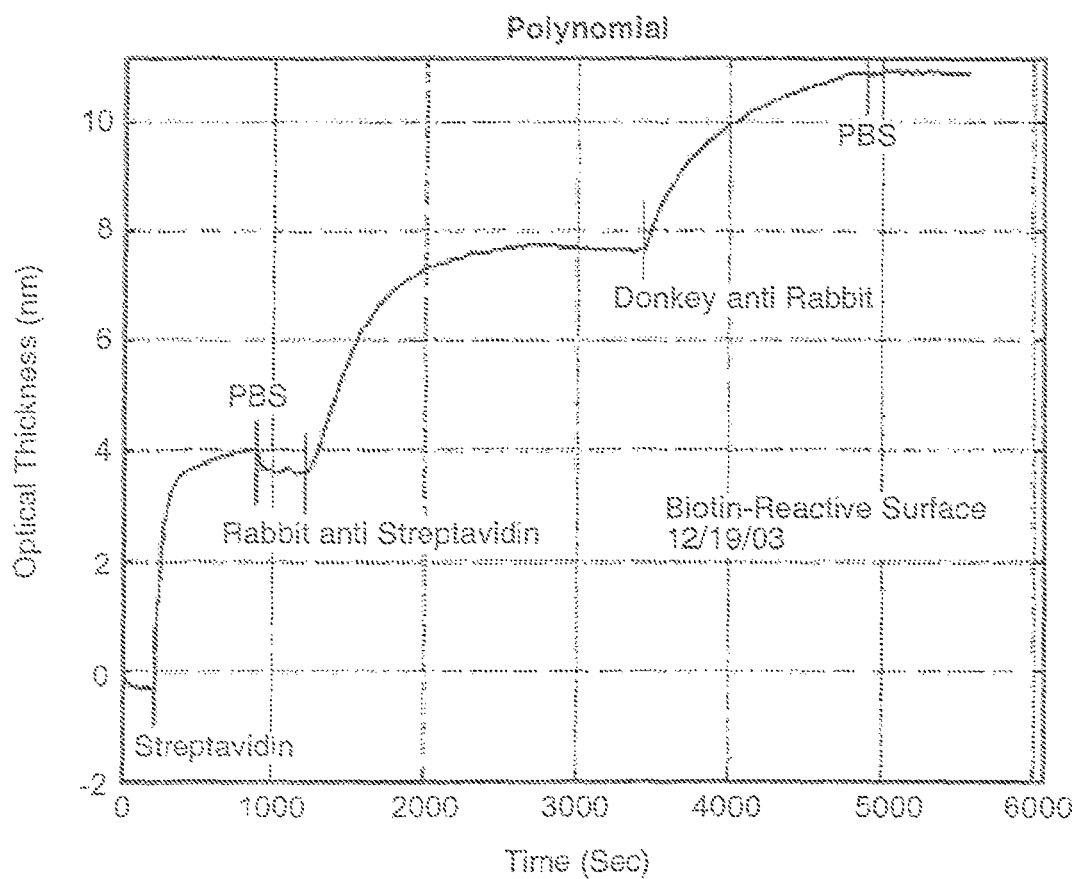
FIG._6

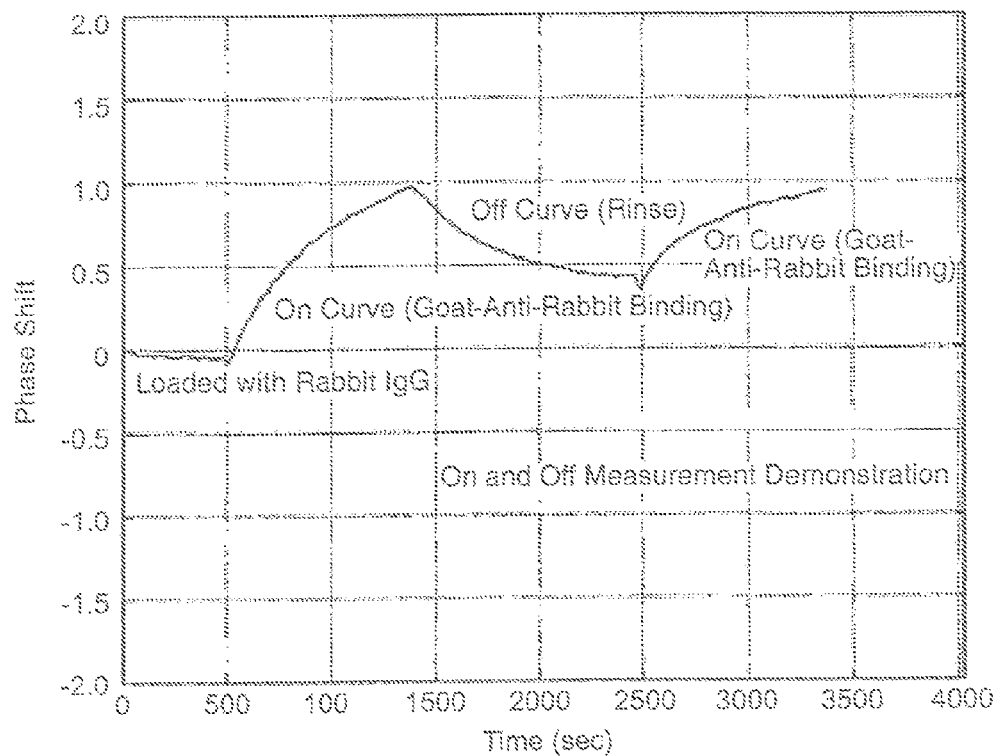
FIG._7
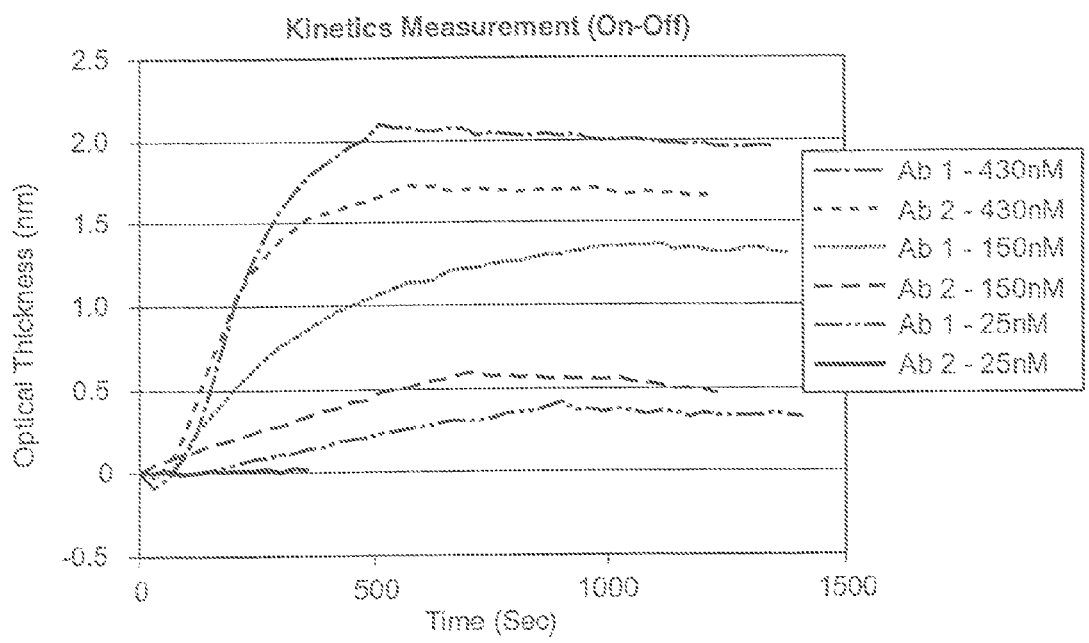
FIG._8

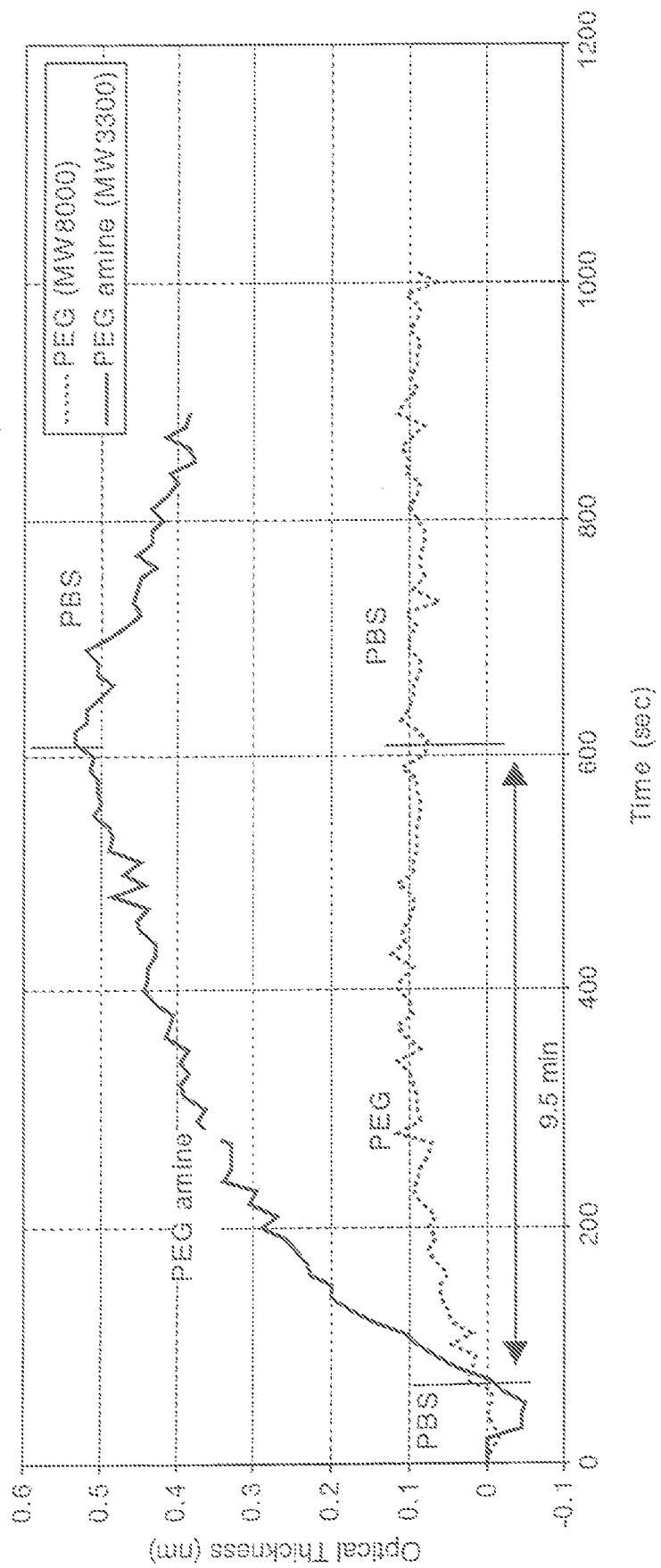
FIG._9

FIBER-OPTIC ASSAY APPARATUS BASED ON PHASE-SHIFT INTERFEROMETRY

CROSS REFERENCE TO RELATED APPLICATIONS

This application is a continuation of U.S. patent application Ser. No. 10/981,901, filed Nov. 4, 2004, entitled "Fiber-Optic Assay Apparatus Based on Phase-Shift Interferometry," which claims the benefit of (1) U.S. Provisional Application No. 60/518,068, filed Nov. 6, 2003, and (2) U.S. Provisional Application No. 60/558,381, filed Mar. 31, 2004, the entire disclosures of which are hereby incorporated by reference in their entireties, including any appendices or attachments thereof, for all purposes.

STATEMENT REGARDING FEDERALLY SPONSORED RESEARCH OR DEVELOPMENT

Not applicable.

BACKGROUND OF THE INVENTION

1. Field of the Invention

The present invention relates to an apparatus and method for detecting the presence, amount, or rate of binding of one or more analytes in a sample, and in particular, to apparatus and method based on fiber optic interferometry.

2. Description of the Related Art

Diagnostic tests based on a binding event between members of an analyte-anti-analyte binding pair are widely used in medical, veterinary, agricultural and research applications. Typically, such methods are employed to detect the presence or amount or an analyte in a sample, and/or the rate of binding of the analyte to the anti-analyte. Typical analyte-anti-analyte pairs include complementary strands of nucleic acids, antigen-antibody pairs, and receptor-receptor binding agent, where the analyte can be either member of the pair, and the anti-analyte molecule, the opposite member.

Diagnostics methods of this type often employ a solid surface having immobilized anti-analyte molecules to which sample analyte molecules will bind specifically and with high affinity at a defined detection zone. In this type of assay, known as a solid-phase assay, the solid surface is exposed to the sample under conditions that promote analyte binding to immobilized anti-analyte molecules. The binding event can be detected directly, e.g. by a change in the mass, reflectivity, thickness, color or other characteristic indicative of a binding event. Where the analyte is pre-labeled, e.g., with a chromophore, or fluorescent or radiolabel, the binding event is detectable by the presence and/or amount of detectable label at the detection zone. Alternatively, the analyte can be labeled after it is bound at the detection zone, e.g., with a secondary, fluorescent-labeled anti-analyte antibody.

Co-owned U.S. Pat. No. 5,804,453, (the '453 patent) which is incorporated herein by reference, discloses a fiber-optic interferometer assay device designed to detect analyte binding to a fiber-optic end surface. Analyte detection is based on a change in the thickness at the end surface of the optical fiber resulting from the binding of analyte molecules to the surface, with greater amount of analyte producing a greater thickness-related change in the interference signal. The change in interference signal is due to a phase shift between light reflected from the end of the fiber and from the binding layer carried on the fiber end, as illustrated particularly in FIGS. 7a and 7b of the '453 patent. The device is simple to operate and provides a rapid assay method for analyte detection.

Ideally, an interferometer assay device will yield readily observable changes in spectral peak and valley (extrema) positions within the range of a conventional visible-light spectrometer, that is, in the visible light range between about 450-700 nm, such that relatively small optical thickness changes at the fiber end can be detected as significant changes in the spectral positions of interference wavelength peaks and valleys. One limitation which has been observed with the device described in the '453 patent is the absence of readily identified wavelength spectral extrema over this spectral range.

The present invention is designed to overcome this limitation, preserving the advantages of speed and simplicity of the earlier-disclosed device, but significantly enhancing sensitivity and accuracy. The present invention also provides a more convenient disposable-head format, as well as a multi-analyte array format, e.g., for gene-chip and protein-chip applications.

SUMMARY OF THE INVENTION

The invention includes, in one aspect, an apparatus for detecting an analyte in a sample, including detecting the presence of analyte, the amount of analyte or the rate of association and/or dissociation of analyte to analyte-binding molecules. The apparatus includes an optical element with a proximal reflecting surface and a distal reflecting surface separated by at least 50 nm. A beam of light from an optical fiber is directed to and reflected from the two reflecting surfaces. The reflected beams are coupled back into the optical fiber and interfere. The optical element also includes a layer of analyte binding molecules that is positioned so that the interference between the reflected beams varies as analyte binds to the layer of analyte binding molecules.

The change in interference can be caused by different physical phenomenon. For example, analyte binding can cause a change in the optical path length or in the physical distance between the two reflecting surfaces. Alternately, analyte binding can cause a change in the index or in the optical absorption of material located between the reflecting surfaces. Analyte binding can also cause the layer of analyte binding molecules to swell, resulting in a change in the interference.

In one particular design, the distal reflecting surface includes the layer of analyte binding molecules. As analyte binds to the layer of analyte binding molecules, the optical path length or the physical distance between the two reflecting surfaces may increase, for example. In another aspect of the invention, a transparent solid material is located between the reflecting surfaces and, optionally, the proximal reflecting surface includes a material with an index greater than that of the transparent solid material. Alternately, an air gap may be located between the reflecting surfaces. In yet another design, the distal reflecting surface is positioned between the proximately reflecting surface and the layer of analyte binding molecules. For example, analyte binding may cause the layer of analyte binding molecules to swell, moving the distal reflecting surface closer to the proximal reflecting surface. In yet another design, the layer of analyte binding molecules is positioned between the two reflecting surfaces. Analyte binding may cause the layer to swell or to change its index, thus changing the interference between the two reflected beams.

In another aspect, the apparatus includes an optical assembly having first and second reflecting surfaces separated by a distance "d" greater than 50 nm. The optical assembly is composed of a transparent optical element that can have a thickness defined between proximal and distal faces of the element of at least 50 nm, preferably between 400-1,000 nm. The first reflecting surface is carried on the distal face of optical element, and is formed of a layer of analyte-binding molecules. The second reflecting surface is formed by a coating of transparent material having an index of refraction greater than that of the optical element. This coating can be formed of a $Ta_2O_5$ layer having a preferred thickness of between 5 and 50 nm. The optical element can be $SiO_2$, and has a thickness of between about 100-5,000 nm, preferably 400-1,000 nm.

Also included are a light source for directing a beam of light onto the first and second reflecting surfaces, and a detector unit that operates to detect a change in the optical thickness of the first reflecting layer resulting from binding of analyte to the analyte-binding molecules, when the assembly is placed in the solution of analyte. The optical thickness change at the first reflecting layer is related to a shift in a phase characteristic of the interference wave formed by the two light waves reflected from said first and second surfaces. This phase characteristic can be a shift in the spectral position(s) of one or more peaks and valleys of the interference wave, or by a change in the period of a full cycle of the wave.

The light source can include an optical fiber having a distal end adapted to be placed adjacent the second reflecting surface in the assembly, and the apparatus further includes an optical coupling for directing reflected light waves reflected from the assembly to the detector.

In a first embodiment, the optical assembly is fixedly mounted on the optical fiber, with the distal end of the optical fiber in contact with the second reflecting surface. In a second embodiment, the optical assembly further includes a second transparent optical element having an index of refraction less than that of the second coating and a thickness greater than about 100 nm, where the coating of high index of refraction material is sandwiched between the two transparent optical elements. In this latter embodiment, the assembly is removably attached to the distal end region of the fiber with a spacing of less than 100 nm or greater than 2 μm between the distal end of the fiber and the confronting face of the second transparent optical element in the assembly.

For detecting multiple analytes, such as multiple nucleic acid species, the layer of analyte-binding molecules can be composed of an array of discrete analyte-binding regions, such as single strands of nucleic acid. The regions are effective to bind different analytes. The optical fiber includes a plurality of individual fibers, each aligned with one of the regions, the detector includes a plurality of detection zones, and the optical coupling functions to couple each of the plurality of fibers with one of the zones.

The analyte-binding molecules in the assembly can be, for example, (i) an anti-species antibody molecules, for use in screening hybridoma libraries for the presence of secreted antibody, (ii) antigen molecules, for use in detecting the presence of antibodies specific against that antigen; (iii) protein molecules, for use in detecting the presence of a binding partner for that protein; (iv) protein molecules, for use in detecting the presence of multiple binding species capable of forming a multi-protein complex with the protein; or (v) single stranded nucleic acid molecules, for detecting the presence of nucleic acid binding molecules.

The detector can be a spectrometer for measuring reflected light intensity over a selected range of wavelengths. Alternatively, or in addition, the light source can include a plurality of light-emitting diodes, each with a characteristic spectral frequency, and the detector functions to record light intensity of reflected light at each of the different LED frequencies. In still another embodiment, the light source includes a white-light source and the detector is designed to record light intensity of reflected light at each of a plurality of different wavelengths.

In another aspect, the invention includes a method for detecting the presence or amount of an analyte in a sample solution. The method involves reacting the sample solution with a first reflecting surface formed by a layer of analyte-binding molecules carried on the distal surface of a transparent optical element having a thickness of at least 50 nm, thereby to increase the thickness of the first reflecting layer by the binding of analyte to the analyte-binding molecules in the layer. The change in thickness of the first reflecting layer is measured by detecting a shift in a phase characteristic of the interference wave formed by the two light waves reflected from the first layer and from a second reflecting layer that is formed on the opposite, proximal surface of the optical element and which has an index of refraction greater than that of the optical element.

The detecting step can include directing light from an optical fiber onto the two reflecting surfaces, and directing reflected light from the two surfaces onto a detector through an optical coupling. The detector can be a spectrometer, where the detecting includes measuring a shift in the spectral position of one or more of the interference extrema produced by the two reflecting lightwaves.

Where the method is used for measuring the rate of association of analyte to the second layer, the reacting step can be carried out until a near-maximum increase in thickness of the first reflecting layer is observed. Where the method is used for measuring the rate of dissociation of analyte to the second layer, the reacting steps can include immersing the second layer in a dissociation buffer for a period of time until a decrease in thickness of the first reflecting layer is observed. Where the method is used for measuring the amount of analyte present in the sample, the detecting is carried out over a period sufficient to measure the thickness of the first reflecting layer at a plurality of different time points.

Where the method is used measuring one or more of a plurality of analytes in a sample, the first reflecting layer is composed of an array of discrete analyte-binding regions, the different regions being effective to bind different analytes, and the detecting is effective to detect a change in the thickness of each of the regions resulting from binding of analyte to the analyte-binding molecules.

These and other objects and features of the present invention will become more fully apparent when the following detailed description of the invention is read in conjunction with the accompanying drawings.

BRIEF DESCRIPTION OF THE SEVERAL VIEWS OF THE DRAWING

These and other features, aspects, and advantages of the present invention will become better understood with regard to the following description, and accompanying drawings, where:

FIG. 1 shows the basic system setup for the bioprobe and its apparatus;

FIG. 2 shows an optical assembly formed accordance to one embodiment of the invention;

FIGS. 3A and 3B show a portion of an interference wave over 7 peak and valley orders (3A), and over in a visible portion of the spectrum (3B);

FIG. 4 shows an optical assembly constructed according to another embodiment of the invention;

FIG. 5 shows a disposable multi-analyte optical assembly having an analyte-binding array and constructed according to another embodiment of the invention;

FIG. 6 shows a sequential binding of three molecules;

FIG. 7 shows on and off curves generated from the association and dissociation of antibodies;

FIG. 8 shows the curves of two antibodies binding to their antigen at different concentrations;

FIG. 9 shows immobilization of bis amino PEG (MW 3300) specifically through an amide bond formation. The PEG (MW 8000) is used as a negative control to monitor non-specific binding of the PEG polymer.

DETAILED DESCRIPTION OF THE INVENTION

Definitions

Figure 10:
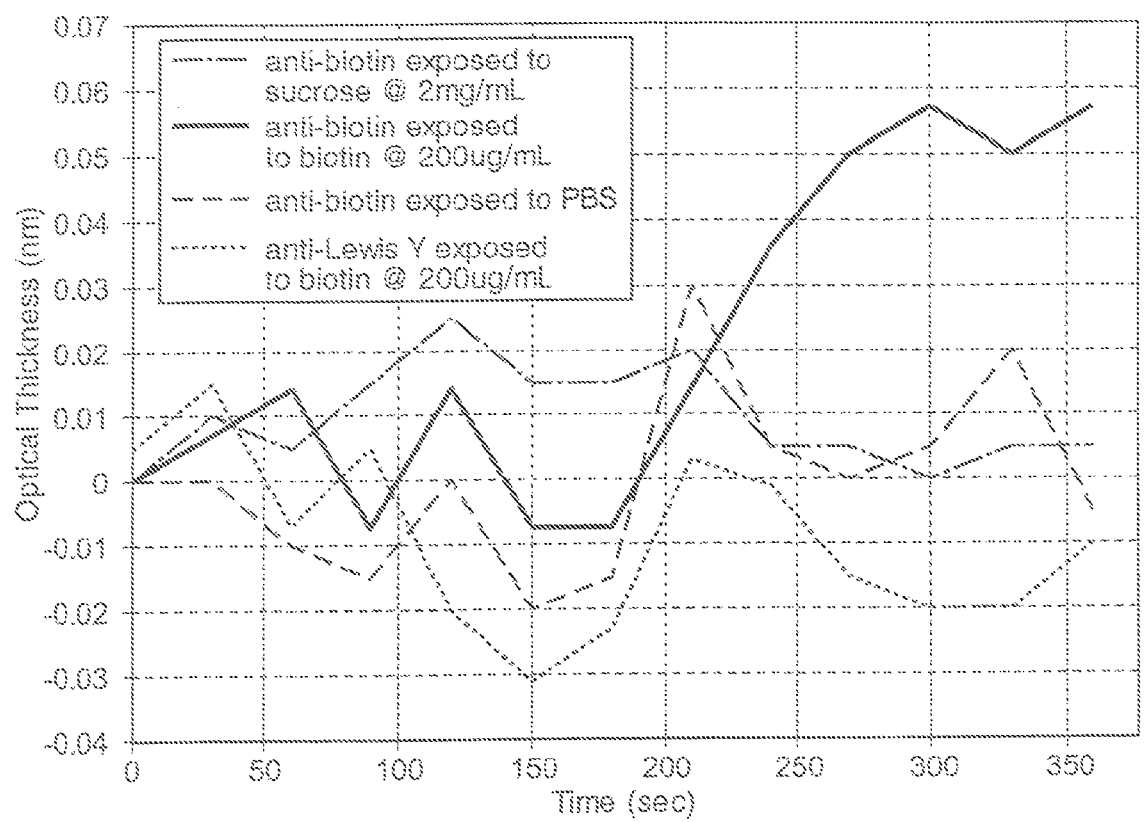
FIG. 10 shows a small molecule binding to a large molecule, negative controls and the base line measurement.

Terms used in the claims and specification are to be construed in accordance with their usual meaning as understood by one skilled in the art except and as defined as set forth below. Numeric ranges recited in the claims and specification are to be construed as including the limits bounding the recited ranges.

The term "in vivo" refers to processes that occur in a living organism.

An "analyte-binding" molecule refers to any molecule capable of participating in a specific binding reaction with an analyte molecule. Examples include but are not limited to, e.g., antibody-antigen binding reactions, and nucleic acid hybridization reactions.

A "specific binding reaction" refers to a binding reaction that is saturable, usually reversible, and that can be competed with an excess of one of the reactants. Specific binding reactions are characterized by complementarity of shape, charge, and other binding determinants as between the participants in the specific binding reaction.

An "antibody" refers to an immunoglobulin molecule having two heavy chains and two light chains prepared by any method known in the art or later developed and includes polyclonal antibodies such as those produced by inoculating a mammal such as a goat, mouse, rabbit, etc. with an immunogen, as well as monoclonal antibodies produced using the well-known Kohler Milstein hybridoma fusion technique. The term includes antibodies produced using genetic engineering methods such as those employing, e.g., SCID mice reconstituted with human immunoglobulin genes, as well as antibodies that have been humanized using art-known resurfacing techniques.

An "antibody fragment" refers to a fragment of an antibody molecule produced by chemical cleavage or genetic engineering techniques, as well as to single chain variable fragments (SCFvs) such as those produced using combinatorial genetic libraries and phage display technologies. Antibody fragments used in accordance with the present invention usually retain the ability to bind their cognate antigen and so include variable sequences and antigen combining sites.

A "small molecule" refers to an organic compound having a molecular weight less than about 500 daltons. Small molecules are useful starting materials for screening to identify drug lead compounds that then can be optimized through traditional medicinal chemistry, structure activity relationship studies to create new drugs. Small molecule drug compounds have the benefit of usually being orally bioavailable. Examples of small molecules include compounds listed in the following databases: MDL/ACD (http://www.mdli.com/), MDL/MDDR (http://www.mdli.com/), SPECS (http://www.specs.net/), the China Natural Product Database (CNPD) (http://www.neotrident.com/), and the compound sample database of the National Center for Drug Screening (http://www.screen.org.cn/).

Abbreviations used in this application include the following: "ss" refers to single-stranded; "SNP" refers to single nucleotide polymorphism; "PBS" refers to phosphate buffered saline (0.01 M phosphate buffer, 0.0027 M potassium chloride and 0.137 M sodium chloride, pH 7.4); "NHS" refers to N-hydroxysuccinimide; "MW" refers to molecular weight; "Sulfo-SMCC" refers to sulfosuccinimidyl 4-[N-maleimidomethyl]cyclohexane-1-carboxylate.

It must be noted that, as used in the specification and the appended claims, the singular forms "a," "an" and "the" include plural referents unless the context clearly dictates otherwise.

Advantages and Utility

The advantages and utility of the invention are illustrated by reference to the Figures and Examples as described in greater detail below. These include the ability to monitor in real time analyte binding reactions without the use of labels, diminishing cost and potential toxicity. A further advantage includes the ability to practice the method using visible wavelength light sources. Yet other advantages are provided by the fiber optic nature of the detector tip that allows binding reactions to be monitored in very small sample volumes, including in "in vitro" spaces, and to bundle fibers to carry out highly multiplexed analyses of binding reactions.

FIG. 1 shows, in schematic view, an interferometer apparatus 20 constructed in accordance with the invention. In its most basic elements, the apparatus includes a light source 22, an optical assembly 26 that functions as a sensing element or detector tip and that will be detailed further with respect to FIGS. 2, 4 and 5 below, and a detector unit 28 for detecting interference signals produced by interfering light waves reflected from the optical assembly 26.

Light from source 22 is directed onto the optical assembly 26, and reflected back to the detector through an optical coupling assembly indicated by dashed lines at 30. In a preferred embodiment, the coupling assembly includes a first optical waveguide or fiber 32 extending from the light source to the optical assembly, a second optical waveguide or fiber 34 which carries reflected light from the optical assembly to the detector, and an optical coupler 36 which optically couples fibers 32, 34. Suitable optical fiber and coupling components are detailed in the above-cited '453 patent. One exemplary coupler is commercially available from many vendors including Ocean Optics (Dunedin, Fla.).

Alternatively, the coupling assembling can include a lens system constructed to focus a light beam onto the upper surface of the optical assembly and to direct reflected interfering light from the optical assembly to the detector. The latter system would not require optical fibers, but would impose relatively stringent requirements on the positioning of the lens elements used for the optical coupling.

The light source in the apparatus can be a white light source, such as a light emitting diode (LED) which produces light over a broad spectrum, e.g., 400 nm or less to 700 nm or greater, typically over a spectral range of at least 100 nm. Alternatively, the light source can be a plurality of sources each having a different characteristic wavelength, such as LEDs designed for light emission at different selected wavelengths in the visible light range. The same function can be achieved by a single light source, e.g., white light source, with suitable filters for directing light with different selected wavelengths onto the optical assembly.

The detector is preferably a spectrometer, such as charge-coupled device (CCD), capable of recording the spectrum of the reflected interfering light from the optical assembly. Alternatively, where the light source operates to direct different selected wavelengths onto the optical assembly, the detector can be a simple photodetector for recording light intensity at each of the different irradiating wavelengths. In still another embodiment, the detector can include a plurality of filters which allows detection of light intensity, e.g., from a white-light source, at each of a plurality of selected wavelengths of the interference reflectance wave. Exemplary light source and detector configurations are described in the above-cited '453 patent, particularly with respect to FIGS. 8 and 10 of that patent, and it will be understood that these configurations are suitable for use in the present invention.

FIG. 2 shows an optical assembly 26 constructed in accordance with one embodiment of the invention, and an adjoining portion of the distal end region of an optical fiber 32 to which the optical assembly is fixedly attached. As seen, the assembly 26 includes a transparent optical element 38 having first and second reflecting surfaces 42, 40 formed on its lower (distal) and upper (proximal) end faces, respectively. According to an important feature of the invention, the thickness "d" of the optical element between its distal and proximal surfaces, i.e., between the two reflecting surfaces, is at least 50 nm, and preferably at least 100 nm. An exemplary thickness is between about 100-5,000 nm, preferably 400-1,000 nm. The first reflecting surface 42 is formed of a layer of analyte-binding molecules, such as molecules 44, which are effective to bind analyte molecules 46 specifically and with high affinity. That is, the analyte and anti-analyte molecules are opposite members of a binding pair of the type described above, which can include, without limitations, antigen-antibody pairs, complementary nucleic acids, and receptor-binding agent pairs.

The index of refraction of the optical element is preferably similar to that of the first reflecting surface, so that reflection from the lower distal end of the end optical assembly occurs predominantly from the layer formed by the analyte-binding molecules, rather than from the interface between the optical element and the analyte-binding molecules. Similarly, as analyte molecules bind to the lower layer of the optical assembly, light reflection form the lower end of the assembly occurs predominantly from the layer formed by the analyte-binding molecules and bound analyte, rather than from the interface region. One exemplary material forming the optical element is $SiO_2$, e.g., a high-quality quality glass having an index of refraction of about 1.4-1.5. The optical element can also be formed of a transparent polymer, such as polystyrene or polyethylene, having an index of refraction preferably in the 1.3-1.8 range.

The second reflecting surface in the optical assembly formed as a layer of transparent material having an index of refraction that is substantially higher than that of the optical element, such that this layer functions to reflect a portion of the light directed onto the optical assembly. Preferably, the second layer has a refractive index greater than 1.8. One exemplary material for the second layer is $Ta_2O_5$ with refractive index equal to 2.1. The layer is typically formed on the optical element by a conventional vapor deposition coating or layering process, to a layer thickness of less than 50 nm, typically between 5 and 30 nm.

The thickness of the first (analyte-binding) layer is designed to optimize the overall sensitivity based on specific hardware and optical components. Conventional immobilization chemistries are used in chemically, e.g., covalently, attaching a layer of analyte-binding molecules to the lower surface of the optical element. For example, a variety of bifunctional reagents containing a siloxane group for chemical attachment to $SiO_2$, and an hydroxyl, amine, carboxyl or other reaction group for attachment of biological molecules, such as proteins (e.g., antigens, antibodies), or nucleic acids. It is also well known to etch or otherwise treat glass a glass surface to increase the density of hydroxyl groups by which analyte-binding molecules can be bound. Where the optical element is formed of a polymer, such as polystyrene, a variety of methods are available for exposing available chemically-active surface groups, such as amine, hydroxyl, and carboxyl groups.

The analyte-binding layer is preferably formed under conditions in which the distal surface of the optical element is densely coated, so that binding of analyte molecules to the layer forces a change in the thickness of the layer, rather than filling in the layer. The analyte-binding layer can be either a monolayer or a multi-layer matrix.

The measurement of the presence, concentration, and/or binding rate of analyte to the optical assembly is enabled by the interference of reflected light beams from the two reflecting surfaces in the optical assembly. Specifically, as analyte molecules attach to or detach from the surface, the average thickness of the first reflecting layer changes accordingly. Because the thickness of all other layers remains the same, the interference wave formed by the light waves reflected from the two surfaces is phase shifted in accordance with this thickness change.

Assume that there are two reflected beams: The first beam is reflected from the first surface, which is the distal end interface between analyte-binding molecules and bound analyte and the surrounding medium; and the second beam is reflected from the second surface, which is the proximal interface between the optical element (the first layer) and the high-index of refraction layer (the second layer). The overall wavelength-dependent intensity of the interference wave is:

$$I = I_1 + I_2 + 2\sqrt{I_1 I_2} \cos\left(\frac{2\pi\Delta}{\lambda}\right)$$

where I is the intensity, $I_1$ and $I_2$ are the intensity of two interference beams, $\Delta$ is the optical path difference, and $\lambda$ is the wavelength.

When $(2\pi\Delta/\lambda)=N\pi$, the curve is at its peak or valley if N is an integer 0, 1, 2, . . . .

The thickness of the first layer $d=\Delta/2n$. Therefore, $\lambda=4nd/N$ at peaks or valleys (extrema).

For the first several values of N, i.e., 0, 1, 2, . . . 7, and assuming a d of 770 nm, the equation gives:

N=0: $\lambda=\infty$ (peak)

N=1: $\lambda=4nd=4,496.80$ nm (Valley)

N=2: $\lambda=2nd=2,248.40$ nm (Peak)

N=3: $\lambda=4nd/3=1,498.9$ nm (Valley)

N=4: $\lambda=nd=1,124.20$ nm (Peak)

N=5: $\lambda=4nd/5=899.36$ nm (Valley)

N=6: $\lambda=2nd/3=749.47$ nm (Peak)

N=7: $\lambda=4nd/7=642$ nm (Valley)

N=8: $\lambda=nd/2=562$ nm (Peak)

N=9: $\lambda=4nd/9=499.64$ nm (Valley)

N=10: λ=4nd/10=449.6 nm (Peak)

As can be seen, and illustrated further in FIGS. 3A and 3B, at least three peaks/valleys (N=7-9) occur in the visible spectral range.

If the $7^{th}$ order valley is used to calculate the change in molecular layer thickness, when the molecular layer attached to the first layer increases from 0 nm to 10 nm, the $7^{th}$ order valley will shift to 650.74 nm. Therefore, the ratio between the actual the phase shift of the $7^{th}$ order valley and thickness change equals (650.74-642.40)/10=0.834.

By contrast, if the initial spacing between the two reflecting layers is made up entirely of the analyte-binding molecules on the end of the fiber, assuming a thickness of this layer of 25 nm, then the first order peak will occur at 146 nm, clearly out of the range of the visible spectrum, so that the device will only see a portion of the region between the O-order valley and the first order peak, but will not see any peaks, making a shift in the spectral characteristics of the interference wave difficult to measure accurately.

Not until the total thickness of the reflecting layer approaches about 100 nm will the first-order peak appear in the visible spectrum. Assuming a total thickness change of up to 50 nm, the thickness of the optical element can then be as small as 50 nm, but is preferably on the order of several hundred nm, so that the phase shift or change in periodicity of the interference wave can be measured readily by a shift in the spectral positions of higher-order peaks or valleys, e.g. where N=3–10.

The ratio between the actual thickness and the measured phase shift is considered as a key factor of measurement sensitivity. It can be appreciated how one can adjust the thickness of the optical element and its refractive index to improve and optimize the sensitivity to accommodate the electronics and optical designs.

FIG. 4 shows an optical assembly 50 that is removably carried on the distal end of an optical fiber 52 in the assay apparatus. The optical element includes a plurality of flexible gripping arms, such as arms 54, that are designed to slide over the end of the fiber and grip the fiber by engagement of an annular rim or detente 56 on the fiber with complementary-shaped recesses formed in the arms, as shown. This attachment serves to position the optical assembly on the fiber to provide an air gap 58 between the distal end of the fiber and the confronting (upper) face of the assembly, of less than 100 nm or greater than 2 μm. With an air gap of greater than about 100 nm, but less that 2 μm, internal reflection from the upper surface of the optical assembly can contribute significantly to undesirable fringes that can adversely impact the detection accuracy.

With continued reference to FIG. 4, the optical assembly includes a first optical element 60 similar to optical element 38 described above, and having first and second reflective layers 62, 64, respectively, corresponding to above-described reflective layers 40, 42, respectively. The assembly further includes a second optical element 66 whose thickness is preferably greater than 100 nm, typically at least 200 nm, and whose index of refraction is similar to that of first optical element 60. Preferably, the two optical elements are constructed of the same glass or a polymeric material having an index of refraction of between about 1.4 and 1.6. Layer 64, which is formed of a high index of refraction material, and has a thickness preferably less than about 30 nm, is sandwiched between the 2 optical elements as shown.

In operation, the optical assembly is placed over the distal fiber end and snapped into place on the fiber. The lower surface of the assembly is then exposed to a sample of analyte, under conditions that favor binding of sample analyte to the analyte-binding molecules forming reflective layer 62. As analyte molecules bind to this layer, the thickness of the layer increases, increasing the distance "d" between reflective surfaces 62 and 64. This produces a shift in the extrema of the interference wave produced by reflection from the two layers, as described above with reference to FIGS. 3A and 3B. This shift in extrema or wavelength, or wavelength period, in turn, is used to determine the change in thickness at the lower (distal-most) reflecting layer. After use, the optical assembly can be removed and discarded, and replaced with fresh element for a new assay, for assaying the same or a different analyte.

FIG. 5 illustrates an optical assembly and fiber bundle in an embodiment of the invention designed for detecting one or more of a plurality of analytes, e.g. different-sequence nucleic acid analytes, in a sample. A fiber bundle 72 is composed of an array, e.g., circular array, for individual optical fibers, such as fibers 74. The optical assembly, indicated generally at 70, is composed of the basic optical elements described above with reference to FIG. 4, but in an array format. Specifically, a first optical element 80 in the element provides at its lower distal surface, an array of analyte-reaction regions, such as regions 84, each containing a layer of analyte-binding molecules effective to bind to one of the different analytes in the sample. Each region forms a first reflective layer in the optical assembly. One preferred sensing provides an array of different-sequence nucleic acids, e.g., cDNAs or oligonucleotides, designed to hybridize specifically with different-sequence nucleic acid analyte species in a sample. That is, the array surface forms a "gene chip" for detecting each of a plurality of different gene sequences.

Also included in the optical assembly are a second optical element 78 and a layer 79 of high index of refraction material sandwiched between the two optical elements, and which provides the second reflecting surface in the optical assembly. The assembly is carried on the fiber bundle 72 by engagement between a pair of flexible support arm, such as arm 76 and an annular rim or detente 86 on the bundle. With the assembly placed on the fiber bundle, the lower distal ends of the fibers are spaced from the confronting surface of optical element 78 by an air gap 85 whose spacing is preferably less than 100 nm or greater than 2 μm. Further, each of the fibers is aligned with a corresponding assay region of the optical assembly, so that each fiber is directing light on, and receiving reflected light from, its aligned detection region. Similarly, the optical coupler in the apparatus, which serves to couple multiple fibers to the detector, preserves the alignment between the array regions and corresponding positions on an optical detector, e.g., two-dimensional CCD. The materials and thickness dimensions of the various optical-assembly components are similar to those described above with respect to FIG. 4.

The apparatus described in this invention can be used more specifically for the following applications:

(i) with an anti-species antibody carried on the tip, for screening hybridoma expression lines for cell lines with high antibody expression;

(ii) with an antigen carried on the tip, to characterize high affinity antibodies against that antigen;

(iii) with a protein carried on the tip, for identifying and characterizing binding partners (DNA, RNA, proteins, carbohydrates, organic molecules) for that protein;

(iv) with a carbohydrate or glycosyl moiety carried on the tip, for identifying and characterizing binding partners (such as, e.g., DNA, RNA, proteins, carbohydrates, organic molecules) for that carbohydrate;

(v) with a protein thought to participate in a multi-protein complex carried on the tip, for characterizing the binding components and/or kinetics of complex formation;

(vi) with a small protein-binding molecule carried on the tip, for identifying and characterizing protein binders for that molecule;

(vii) with an antibody carried on the tip, for constructing a calibration curve for the analyte using a set of analytes standards. Using this calibration curve, one can then determine the concentration of the analyte in unknown solutions (cell culture supernatants, biological samples, process mixtures, etc).

(viii) with a single-stranded nucleic acid, e.g. ssDNA or RNA carried on the tip, for identifying and molecules that bind specifically to the nucleic acid.

Using a temperature control block, the apparatus and method can also be used to monitor the binding and characterize the binding of an immobilized ssDNA to an oligonucleotide in solution to perform SNP analysis.

The following examples illustrate various methods and applications of the invention, but are in no way intended to limit its scope.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, Biochemistry (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ Ed. (Plenum Press) Vols A and B (1992).

Example 1

Small Molecule-Protein Binding Reaction

This example demonstrates the capability to detect the binding of protein to small molecule immobilized on a sensor tip and subsequent bindings of multiple antibodies. The two-layer configuration on the tip of an optic fiber is used for this test. The thickness of the first $Ta_2O_5$ layer is 25 nm and the thickness of the second $SiO_2$ layer is 770 nm. The fiber was purchased from Ocean Optics (Dunedin, Fla.). It was manually cut into segments that are 40 mm long. Both ends of these segments were polished to standard mirror surface quality. The polishing method used here was exactly the same as those for optical lenses and mirrors. One surface of these fiber segments was outsourced to an optical coating house for $Ta_2O_5$ layer and $SiO_2$ layer. This vendor employed an ion-beam assisted physical vapor deposition (IAPVD) coater made by Leybold. IAPVD is a commonly used coating technique for anti-reflection and optical filters. The experimental steps included the following (all steps are performed at room temperature unless otherwise noted):

The fiber tip was coated with a polymer monolayer derivatized with biotin. The polymer monolayer was prepared using a biotinylated lipid (custom). This lipid was using to form a lipid monolayer on the surface of water solution. The monolayer was cross linked using UV light for 15 minutes. Clean, dry fibers were then brought in contact with the floating thin film and the biotin polymer was adsorbed onto the fiber tip. The fibers were then dryed at 60° C. for 1 hour. The fiber were then stored under ambient conditions The biosensor tip was immersed in 50 µg/ml streptavidin streptavidin (Pierce Biotechnology, Rockford Ill., cat #21122) in PBS (Invitrogen, Carlsbad, Calif.; cat #14190078) for 9 minutes and then rinsed briefly with PBS.

The same tip was dipped into 10 µg/ml rabbit-anti-streptavidin solution (AbCam, Cambridge, Mass.; cat #ab6676-1000) in PBS for 36 minutes and then washed with PBS briefly.

Finally, the tip was immersed in 50 µg/mL donkey-anti-rabbit antibody solution antibody (Jackson ImmunoResearch, West Grove, Pa.; cat# 711-005-152) in PBS for 25 minutes. A final 10 minute rinse was performed in PBS solution.

FIG. 6 shows the real-time response curve for this sequential binding test. The vertical axis is the $7^{th}$ order valley phase shift in nanometers. It clearly shows the binding of streptavidin to the biotin already immobilized on the tip, and subsequent bindings of anti-streptavidin antibody to streptavidin and a second antibody to this first antibody. The dissociation of the streptavidin layer from the tip was visible (a small reduction in the optical thickness) at 900 seconds.

Example 2

Biomolecular Interaction Analysis of Kinetics and Affinity of Biomolecular Interactions This example illustrates use of the invention to carry out a biomolecular interaction analysis (BIA) measuring kinetics and affinity of biomolecular interactions. The same tip configuration as described in Example 1 was used. The experimental steps included the following (all steps are performed at room temperature unless otherwise noted):

Mercaptosilane coated tips were prepared using the following procedure. Clean, dry fibers were incubated in a mixture of Toluene: hexanoic acid: mercaptopropyltrioxysilane (10:2:1 volumetric ratio) at room temperature for 24 hours. The fibers were rinsed 2× with 10 mL toluene for 5 minutes each. The fibers were then rinsed 1× with 10 mL of ethanol and dried under a stream of argon and stored at ambient conditions.

The biosensor tip was first derivatized by immersion in a with 10 µg/ml solution of rabbit-IgG (Jackson ImmunoResearch, West Grove, Pa.; cat# 309-005-003) in PBS for 1 hour.

The coated tip was dipped into 10 µg/ml goat-anti-rabbit antibody solution (Jackson ImmunoResearch, West Grove, Pa.; cat# 111-005-003) in PBS and remained in it for 15 minutes.

The tip was removed and washed in PBS. To facilitate the dissociation of the second antibody from the first antibody, the PBS was agitated manually for 20 minutes.

The tip was then dipped into the same goat-anti-rabbit solution again to show the reproducible association of goat-anti-rabbit to rabbit-IgG.

FIG. 7 shows the on and off curves generated from the association and dissociation of rabbit-IgG and goat-anti-rabbit. The vertical axis is again the $7^{th}$ order valley phase shift. The phase shift is directly related to the average thickness with a ratio of 0.834. The ability to detect the on and off curves reliably is essential for measuring interaction kinetics and affinity.

Example 3

Calculating Affinity Constants from Antibody-Antigen Binding and Release Curves

This experiment demonstrates the calculation of affinity constants from measuring on and off curves for two antibodies and their antigen. The proprietary antibodies were labeled as Ab-1 and Ab-2. The molecular weight of the antigen was about 30 kilodaltons. The same tip configuration as described in Example 1 was used. The same mercaptosilane fiber preparation as described in Example 2 was used. The experimental steps included (all steps are performed at room temperature unless otherwise noted):

The fiber tip was activated for covalent attachment of the antigen. Mercaptosilane coated fibers were activated by immersing the sensor tips in 50 µL of a 50 mg/mL solution of sulfo-SMCC (Pierce Biotechnology, Rockford Ill.; cat #22322) in DMF (Sigma-Aldrich Chemical Company, St Louis, Mo.; cat #494488) at for 2 hours. The sensor tips were rinsed briefly in DMF and dried;

The antigen was covalently bound to the activated fiber tip by immersing the activated tip in a 20 µg/ml solution of antigen in PBS for 20 minutes. The tip was rinsed with PBS for 2 minutes. Following the PBS rinse, the tip was quenched with an aqueous solution of 100 µM ethanolamine pH 8.5 (Sigma-Aldrich Chemical Company, St Louis, Mo.; cat #E9508) for 5 minutes and then was rinsed again in PBS for 2 minutes.

The same tip was immersed in antibody for an association test and the real-time binding data were recorded for 9-15 minutes (depending on the antibody identity and concentration). Once those data were recorded, the tip was again immersed in PBS and agitated to measure the off curve (i.e., dissociation between the immobilized antigen and bound antibody) for 9-15 minutes. The binding (on curve) and dissociation (off curve) measurements were repeated using different concentrations of antibody (25 nM, 150 nM, and 430 nM) and with two different antibodies identified as Ab-1 and Ab-2.

FIG. 8 shows the association and dissociation curves at different concentrations. The test of 25 nM Ab-2 was not completed because the association was extremely slow at this concentration. These illustrated curves are plots of the raw data.

$K_{on}$, $K_{off}$, and $K_D$ were derived from these curves by fitting the raw data with a first order exponential function. By averaging two sets of data, kinetic and affinity coefficients were obtained as follows:

| Ab-1 | Ab-2 |
|---|---|
| $K_{on} = 1.35 \times 10^5$ $(M^{-1}S^{-1})$ | $K_{on} = 2.01 \times 10^5$ $(M^{-1}S^{-1})$ |
| $K_{off} = 5.55 \times 10^{-5}$ $(S^{-1})$ | $K_{off} = 8.15 \times 10^{-5}$ $(S^{-1})$ |
| $K_D = K_{off}/K_{on} = 3.99 \times 10^{-9}$ (M) | $K_D = K_{off}/K_{on} = 4.45 \times 10^{-9}$ (M) |

Example 4

NHS-Ester Activated Tips

The same tip configuration as described in Example 1 was used. The same mercaptosilane fiber preparation as described in Example 2 was used. Mercaptosilane coated fibers were activated by immersing the sensor tips in 50 µL of a 50 mg/mL solution of sulfo-SMCC (Pierce Biotechnology, Rockford Ill.; cat #22322) in DMF (Sigma-Aldrich Chemical Company, St Louis, Mo.; cat #494488) at for 2 hours. The sensor tips were rinsed briefly in DMF and dried.

Amine containing molecules can be covalently bound to this surface through formation of a stable amide linkage. Molecules that do not contain free amines are not immobilized through the NHS moiety, but these molecules can still bind to the surface through non-specific binding. This non-specific binding can be multi-layered whereas the covalent immobilization through the NHS esters will be in a single layer controlled by the availability and accessibility of the NHS ester.

In this set of experiments, a bis amino PEG (MW 3300) (Shearwater Polymers, San Carlos, Calif.) was used as a test compound to covalently bind to the activated surface. A PEG (MW 8000) (Sigma-Aldrich Chemical Company, St Louis, Mo.; cat #04162) that contained no free amino groups was used as a negative control. This negative control was used to look for any non-specific or multi-layered binding that might be inherent to PEG polymers on this surface.

FIG. 9 shows the time course of the treatment of the activated mercaptosilane tip with the test molecules. The activated tip showed a distinct increase in optical thickness upon exposure to the 0.1 mg/mL bis amino PEG (MW 3300) in PBS. This increase is stopped when the bis amino PEG solution is replaced by the PBS buffer. The activated tip exposed to 0.1 mg/mL PEG (MW8000) in PBS, which contains no amines, shows a small initial increase in optical thickness but the trace quickly becomes flat. From this it can be concluded that the PEG polymer does not have intrinsic non-specific binding and that the binding seen for the bis amino PEG is attributed to the specific covalent immobilization of the amine group.

Example 5

Antibody Derivatized Tips Using NHS-Ester Chemistry

This example illustrates the binding of a low molecular weight molecule binding to an immobilized high molecular weight molecule. Using the same NHS ester terminated surface described in Example 4 and the same tip configuration as described in Example 1, an anti-biotin antibody was immobilized to 3 fibers. Immobilization of the antibody was accomplished by immersing the activated fiber in a 20 µg/mL solution of mouse anti-biotin antibody (Biodesign, Saco Minn.; cat #H61504M) in PBS for 1 hour at room temperature. The tip was rinsed with PBS for 2 minutes. Following the PBS rinse, the tip was quenched with an aqueous solution of 100 µM ethanolamine pH 8.5 (Sigma-Aldrich Chemical Company, St Louis, Mo.; cat #E9508) for 5 minutes and then was rinsed again in PBS for 2 minutes.

The first fiber was exposed to a solution of 200 µg/mL biotin (Pierce Biotechnology, Rockford Ill.; cat #29129) in PBS. Controls using a solution of sucrose (Sigma-Aldrich Chemical Company, St Louis, Mo.; cat #S8501) (2 mg/mL) and PBS were carried out on the second and the third fibers to determine baseline noise. Data from these tests are shown in FIG. 10. Biotin binding is seen as an increase in optical thickness, whereas exposure to sucrose shows no detectable increase over baseline (PBS).

Another negative control was carried out using an irrelevant antibody (anti-Lewis Y antibody from Calbiochem, San Diego Calif.; cat# 434636) immobilized in an identical fashion to the anti-biotin antibody above. This immobilized antibody was exposed to a solution of 200 µg/mL biotin. The lack of biotin binding to this antibody indicates that the biotin binding to the anti-biotin antibody is a result of specific interactions and not due to non-specific binding.

While the invention has been particularly shown and described with reference to a preferred embodiments and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. An optical assembly for use in detecting an analyte in a sample based on interference, comprising:
   an optical fiber having a tip; and
   an optical element removably attached to the tip of the optical fiber and configured for receiving a beam of light from the optical fiber, the optical element comprising flexible gripping arms that slide over and grip the optical fiber to removably attach to optical element to the optical fiber,
   said optical element comprising a transparent material, a first reflecting surface, and a second reflecting surface separated from the first reflecting surface by the transparent material, said first and second reflecting surfaces separated by at least 50 nm,
   wherein said first reflecting surface binds a layer of analyte binding molecules positioned so that interference between a beam of light reflected from the first reflecting surface into the optical fiber and a beam of light reflected from the second reflecting surface into the optical fiber varies as analyte binds to the layer of analyte binding molecules.

2. The assembly of claim 1, wherein said second reflecting surface comprises a layer of material having an index of refraction greater than the refractive index of said transparent material.

3. The assembly of claim 1, wherein the separation between said first and second reflecting surfaces is between 100 nm and 5,000 nm.

4. The assembly of claim 3, wherein the separation between said first and second reflecting surfaces is between 400 nm and 1,000 nm.

5. The assembly of claim 1, wherein the refractive index of said optical element transparent material is less than 1.8.

6. The assembly of claim 5, wherein said optical element transparent material is a material selected from the group consisting of $SiO_2$ and a transparent polymer.

7. The assembly of claim 6, wherein said transparent polymer comprises polystyrene or polyethylene.

8. The assembly of claim 1, wherein the second reflecting surface comprises a layer of material having a refractive index greater than 1.8.

9. The assembly of claim 8, wherein said second reflecting surface layer comprises $Ta_2O_5$.

10. The assembly of claim 9, wherein the thickness of said second reflecting surface layer is between 5 nm and 50 nm.

11. The assembly of claim 1, wherein said layer of analyte binding molecules comprises a molecule selected from the group consisting of a protein, a small molecule, a nucleic acid and a carbohydrate.

12. The assembly of claim 11, wherein said protein is selected from the group consisting of an avidin, a streptavidin, an antibody, and an antibody fragment.

13. The assembly of claim 1, wherein said optical assembly is adapted for coupling to said light source through a mechanical coupling that engages said optical element with said fiber.

14. The assembly of claim 1, wherein said optical element is adapted for coupling to said light source through a coupling assembly that comprises a lens system.

15. The assembly of claim 1, further comprising a second optical element overlaying said second reflecting surface.

16. The assembly of claim 15, wherein the thickness of said second optical element is greater than 100 nm.

17. The assembly of claim 16, wherein the thickness of said second optical element is greater than 200 nm.

18. The assembly of claim 15, wherein said optical assembly is adapted for coupling to said light source through a mechanical coupling that engages said second optical element with said fiber.

19. The assembly of claim 18, wherein said mechanical coupling provides an air gap between said second optical element and said fiber.

20. The assembly of claim 19, wherein said air gap is less than 100 nm.

21. The assembly of claim 19, wherein said air gap is greater than 2 µm.

22. The assembly of claim 1, wherein the optical element is configured for detachment from the optical fiber and disposal after use.

23. A two dimensional array of the assemblies of claim 1.

24. A two dimensional array of the assemblies of claim 15.

25. An apparatus for detecting an analyte, comprising:
   the assembly of claim 1;
   a light source for directing light onto said first and said second reflecting surfaces; and
   a detector that receives light from said first and said second reflecting surfaces and detects a change in optical thickness of said first reflecting surface upon exposure of said first reflecting surface to said analyte.

26. An apparatus for detecting an analyte, comprising:
   the assembly of claim 15;
   a light source for directing light onto said first and said second reflecting surfaces; and
   a detector that receives light from said first and said second reflecting surfaces and detects a change in optical thickness of said first reflecting surface upon exposure of said first reflecting surface to said analyte.

27. An apparatus for detecting an analyte, comprising:
   the two dimensional array of the assemblies of claim 23;
   a light source for directing light onto said first and said second reflecting surfaces; and
   a detector that receives light from said first and said second reflecting surfaces and detects a change in optical thickness of said first reflecting surface upon exposure of said first reflecting surface to said analyte.

28. An apparatus for detecting an analyte, comprising:
   the two dimensional array of the assemblies of claim 24;
   a light source for directing light onto said first and said second reflecting surfaces; and
   a detector that receives light from said first and said second reflecting surfaces and detects a change in optical thickness of said first reflecting surface upon exposure of said first reflecting surface to said analyte.

29. A kit, comprising:

an optical assembly comprising:

an optical fiber having a tip;

an optical element removably attached to the tip of the optical fiber and configured for receiving a beam of light from the optical fiber, the optical element comprising flexible gripping arms that slide over and grip the optical fiber to removably attach to optical element to the optical fiber, said optical element comprising a transparent material, a first reflecting surface, and a second reflecting surface, said second reflecting surface separated from the first reflecting surface by the transparent material, said first and second reflecting surfaces separated by at least 50 nm, wherein said first reflecting surface binds a layer of analyte binding molecules positioned so that interference between a beam of light reflected from the first reflecting surface into the optical fiber and a beam of light reflected from the second reflecting surface into the optical fiber varies as analyte binds to the layer of analyte binding molecules, and said second reflecting surface comprises a layer of material having an index of refraction greater than the refractive index of said transparent material; and instructions for binding said layer of analyte binding molecules to said first reflecting surface.

30. The kit of claim 29, further comprising a reagent for chemically modifying said first surface and instructions for using said reagent.

31. The kit of claim 29, wherein said optical assembly further comprises a second optical element overlaying said second reflecting surface.

32. A method for detecting analyte in a sample, comprising:

providing the apparatus of claim 25 and a sample;

exposing said first reflecting surface to said sample, and determining whether said exposure results in a change in optical thickness of said first reflecting surface.

33. A method for detecting analyte in a sample, comprising:

providing the apparatus of claim 26 and a sample;

exposing said first reflecting surface to said sample, and determining whether said exposure results in a change in optical thickness of said first reflecting surface.

34. A method for detecting analyte in a sample, comprising:

providing the apparatus of claim 27 and a sample;

exposing said first reflecting surface to said sample, and determining whether said exposure results in a change in optical thickness of said first reflecting surface.

35. A method for detecting analyte in a sample, comprising:

providing the apparatus of claim 28 and a sample;

exposing said first reflecting surface to said sample, and determining whether said exposure results in a change in optical thickness of said first reflecting surface.

* * * * *